(12) United States Patent
Kishida

(10) Patent No.: US 10,251,547 B2
(45) Date of Patent: Apr. 9, 2019

(54) OPHTHALMIC APPARATUS, CONTROL METHOD, AND COMPUTER READABLE STORAGE MEDIUM

(71) Applicant: CANON KABUSHIKI KAISHA, Tokyo (JP)

(72) Inventor: Nobuyoshi Kishida, Kashiwa (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/988,181

(22) Filed: Jan. 5, 2016

(65) Prior Publication Data
US 2016/0198945 A1 Jul. 14, 2016

(30) Foreign Application Priority Data

Jan. 8, 2015 (JP) .................................. 2015-002517

(51) Int. Cl.
| | | |
|---|---|---|
| *A61B 3/14* | (2006.01) | |
| *A61B 3/10* | (2006.01) | |
| *A61B 3/00* | (2006.01) | |
| *A61B 3/12* | (2006.01) | |

(52) U.S. Cl.
CPC ............ *A61B 3/102* (2013.01); *A61B 3/0025* (2013.01); *A61B 3/12* (2013.01); *A61B 3/14* (2013.01)

(58) Field of Classification Search
CPC .. A61B 3/12; A61B 3/14; A61B 3/102; A61B 3/0025; A61B 3/0058; A61B 3/0075; A61B 3/1025; G01N 21/4795

USPC ........ 359/206; 351/205, 206, 208, 209, 210, 351/211, 221, 246; 356/497
See application file for complete search history.

(56) References Cited

U.S. PATENT DOCUMENTS

| | | | | |
|---|---|---|---|---|
| 2010/0195050 A1* | 8/2010 | Sakagawa | ................ | A61B 3/12 351/208 |
| 2010/0238403 A1* | 9/2010 | Kobayashi | ........... | A61B 3/0058 351/206 |
| 2011/0299035 A1* | 12/2011 | Suehira | .............. | G01N 21/4795 351/206 |
| 2012/0321166 A1* | 12/2012 | Kitamura | ............. | A61B 3/0058 382/131 |

FOREIGN PATENT DOCUMENTS

| | | |
|---|---|---|
| JP | 2010110391 A | 5/2010 |
| JP | 2010-259629 A | 11/2010 |

* cited by examiner

*Primary Examiner* — Mustak Choudhury
(74) *Attorney, Agent, or Firm* — Canon U.S.A., Inc. IP Division

(57) ABSTRACT

There are included an acquiring unit configured to acquire a parameter regarding capturing of a first tomographic image of an eye to be examined, an acquiring unit configured to acquire a parameter regarding capturing of a second tomographic image of the eye to be examined, wherein capturing of the second tomographic image is being performed after capturing of the first tomographic image, and a warning unit configured to issue a warning against capturing of the second tomographic image in accordance with a comparison between the parameter regarding capturing of the first tomographic image and the parameter regarding capturing of the second tomographic image.

9 Claims, 10 Drawing Sheets

OPHTHALMIC APPARATUS, CONTROL METHOD, AND COMPUTER READABLE STORAGE MEDIUM

BACKGROUND

Field

Aspects of the present disclosure generally relate to an ophthalmic apparatus, a control method, and a program.

Description of the Related Art

An optical coherence tomography (OCT) device is known that is equipped with the function (follow-up function) of capturing images of the same region as an image-capturing region used in the past in order to perform a post-treatment observation for an eye to be examined, by comparing a tomographic image captured in the past and a current tomographic image.

Japanese Patent Laid-Open No. 2010-259629 discloses that in the case where the performance of an OCT device has improved in the process of post-treatment observations and a region where image capturing is capable of being performed has been enlarged, an image-capturing region used this time is automatically set to include an image-capturing region used in the past.

However, it is not stated about how to control image capturing in the case where, for example, an image-capturing region or a resolution regarding image capturing performed this time is inferior to that regarding image capturing performed in the past.

SUMMARY OF THE INVENTION

The disclosed technologies are made in light of these circumstances, and an aspect of the present invention provides appropriate image-capturing control in the case where, for example, an image-capturing region or a resolution regarding image capturing performed this time is inferior to that regarding image capturing performed in the past.

Note that in addition to this, another aspect of the present invention provides advantages derived from structural elements shown in the following embodiments for execution of the invention, the advantages being not obtained in the related art.

The present disclosure provides an ophthalmic apparatus including an acquiring unit configured to acquire a parameter regarding capturing of a first tomographic image of an eye to be examined, an acquiring unit configured to acquire a parameter regarding capturing of a second tomographic image of the eye to be examined, wherein capturing of the second tomographic image is being performed after capturing of the first tomographic image, and a warning unit configured to issue a warning against capturing of the second tomographic image in accordance with a comparison between the parameter regarding capturing of the first tomographic image and the parameter regarding capturing of the second tomographic image.

Further features of the present invention will become apparent from the following description of exemplary embodiments with reference to the attached drawings.

DESCRIPTION OF THE EMBODIMENTS

In the following, an eye-portion image capturing system 10 according to the present embodiment will be described with reference to the attached drawings. Note that configurations illustrated in the following embodiments are mere examples, and the present invention is not limited to the following exemplary embodiments.

First Exemplary Embodiment

In the following embodiment, as an ophthalmic image processing apparatus according to the present invention, an example will be described in which an OCT device is applied that captures an image of a fundus portion of a subject. In addition, in the following embodiments, examples will be described in which a fundus portion is applied as an object; however, the present invention is not limited to these embodiments. For example, an anterior eye portion such as a cornea, a crystalline lens, or an iris may also be applied as an object as long as the object serves as a subject to be imaged in an tomographic image.

Figure 1:
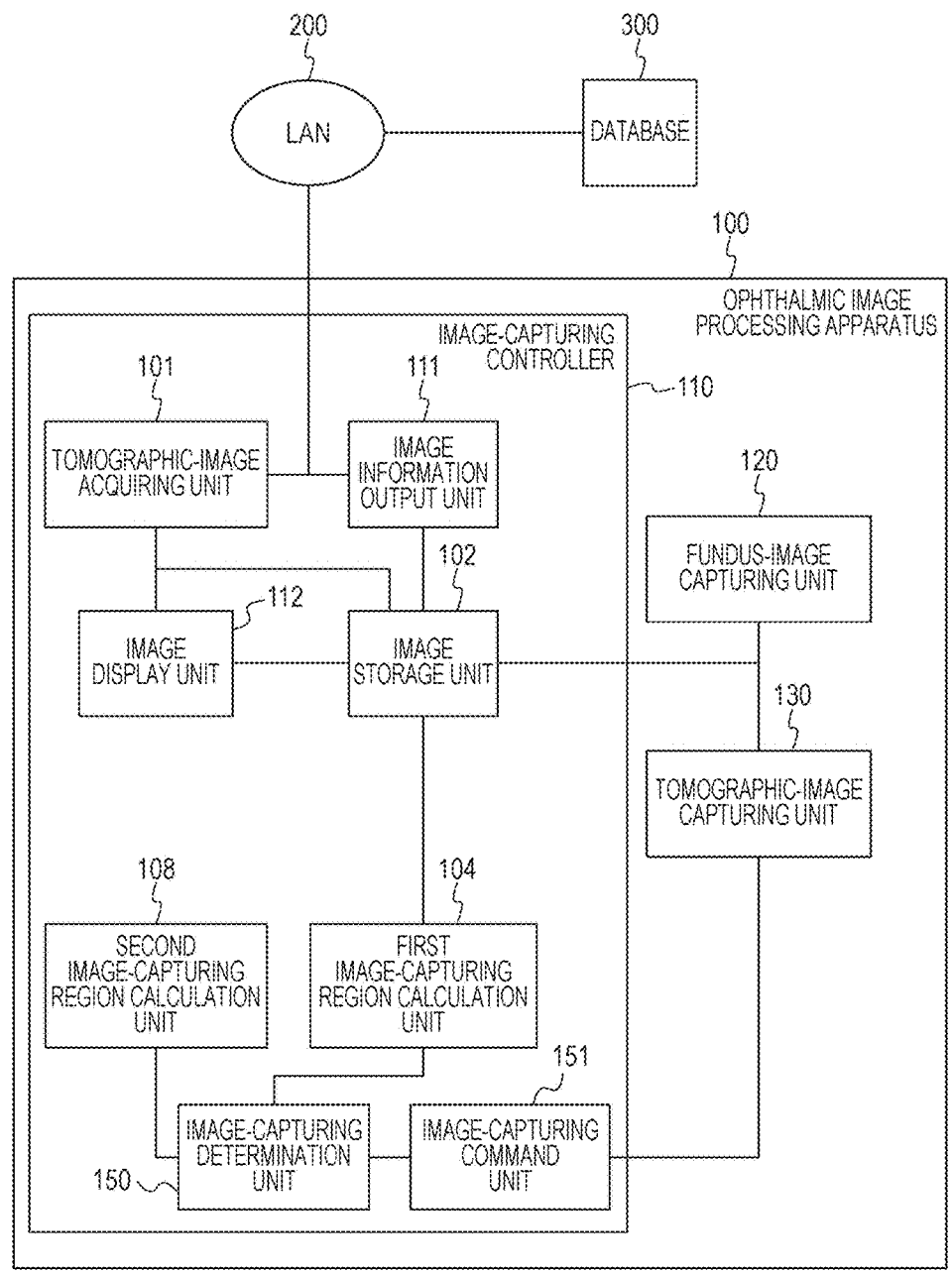
FIG. 1 is a diagram illustrating an example of the configuration of an ophthalmic image processing apparatus according to a first exemplary embodiment.

FIG. 1 is a schematic diagram illustrating an example of a schematic configuration of an eye-portion image capturing system (image processing system) 10 according to a first exemplary embodiment.

The eye-portion image capturing system 10 includes, as illustrated in FIG. 1, an ophthalmic image processing apparatus (ophthalmic apparatus) 100, a local-area network (LAN) 200, and an image database 300. The ophthalmic image processing apparatus 100 is connected to the image database 300, which stores images captured in the past, via the LAN 200. That is, the ophthalmic image processing apparatus 100 is configured to be able to acquire an image captured in the past from the image database 300, and also to save a captured image in the image database 300 as an image captured in the past.

The ophthalmic image processing apparatus 100 includes, as illustrated in FIG. 1, an image-capturing controller 110, a fundus-image capturing unit 120, and a tomographic-image capturing unit 130.

In addition, the image-capturing controller 110 includes, as illustrated in FIG. 1, a tomographic-image acquiring unit 101, an image storage unit 102, a first image-capturing region calculation unit 104, and a second image-capturing region calculation unit 108. Furthermore, the image-capturing controller 110 includes, as illustrated in FIG. 1, an image-capturing determination unit 150, an image-capturing command unit 151, an image information output unit 111, and an image display unit 112. The image display unit 112 is a monitor that displays various types of information, and includes, for example, a liquid crystal display (LCD).

The fundus-image capturing unit 120 captures a fundus image of an eye portion of a subject using, for example, a scanning laser ophthalmoscope (SLO). Note that in this example, the fundus-image capturing unit 120 captures fundus images using an SLO; however, the fundus-image capturing unit 120 may be, for example, a fundus camera capturing fundus images by performing an infrared (IR) observation or the like.

The tomographic-image capturing unit 130 captures a tomographic image of an eye portion of a subject. Note that in this example, the tomographic-image capturing unit 130 captures tomographic images using a spectral-domain OCT device; however, the tomographic-image capturing unit 130 may also capture tomographic images using other methods (for example, a time-domain method or a swept-source method).

The fundus-image capturing unit 120 and the tomographic-image capturing unit 130 are connected to each other, and are configured to be able to capture tomographic images while capturing fundus images at all times. Specifically, the fundus-image capturing unit 120 and the tomographic-image capturing unit 130 are configured to be able to capture a tomographic image at an arbitrary position on a fundus image by controlling the positional relationship between lasers used in respective types of image capturing.

The tomographic-image acquiring unit 101 acquires an image captured in the past from the image database 300 and stores, in the image storage unit 102, the image captured in that past. Here, tomographic images captured in the past and acquired from the image database 300 by the tomographic-image acquiring unit 101 are referred to as first tomographic images. Note that, for example, images captured by tomographic-image capturing units other than the tomographic-image capturing unit 130 may also be applied as first tomographic images. In this exemplary embodiment, suppose that first tomographic images are captured using a swept-source OCT device having a wider image-capturing range (image-capturing angle of view) than a spectral-domain OCT device. Note that the image-capturing method for first tomographic images is not limited to the swept-source method, and may also be a time-domain method or a spectral-domain method.

The image storage unit 102 stores images captured in the past and acquired by the tomographic-image acquiring unit 101, and also stores fundus images captured by the fundus-image capturing unit 120 and tomographic images captured by the tomographic-image capturing unit 130. For example, the image storage unit 102 includes a hard disk drive (HDD), a solid-state disk (SSD), or the like.

The first image-capturing region calculation unit 104 calculates the position of an image-capturing region (first image-capturing region) for an image captured in the past from the images stored in the image storage unit 102, and outputs information regarding this position to the image-capturing determination unit 150. That is, the first image-capturing region calculation unit 104 is an example of a first acquiring unit that acquires a parameter regarding capturing of a first tomographic image of an eye to be examined. Note that in the case where image-capturing regions themselves for images captured in the past are stored in the image storage unit 102, the first image-capturing region calculation unit 104 does not need to refer to the images. Alternatively, for example, the first image-capturing region calculation unit 104 may calculate an image-capturing region for images captured in the past by performing matching between an integrated image obtained by integrating tomographic images captured in the past and a fundus image captured in the past or a current fundus image. In the case where matching is performed between a current fundus image and an integrated image, an image-capturing region calculated by the second image-capturing region calculation unit 108 this time may be easily compared with an image-capturing region for images captured in the past.

The image-capturing region for this image captured in the past is, for example, an image-capturing range of an OCT device centered around a macula lutea portion of a fundus, and thus the image-capturing region for this image captured in the past is able to be calculated by reading image-capturing range information recorded in the image captured in the past. In addition, the image-capturing region for this image captured in the past is able to be calculated using the position information regarding a fundus image and a tomographic image among images captured in the past.

The second image-capturing region calculation unit 108 calculates a second image-capturing region using, for example, information regarding the maximum image-capturing size in which image capturing is possible using the tomographic-image capturing unit 130. That is, the second image-capturing region calculation unit 108 is an example of a second acquiring unit that acquires, after capturing of a first tomographic image, a parameter regarding capturing of a second tomographic image of an eye to be examined. Note that the information regarding the maximum image-capturing size is prestored in, for example, a storage unit such as the image storage unit 102. Here, an image-capturing region having a size smaller than or equal to the maximum image-capturing size in which image capturing is possible may be set as the second image-capturing region, and the image-capturing position of the second image-capturing region may be changed using an input unit, which is not illustrated, operated by an operator. In this case, the image-capturing region input by the operator is acquired by the second image-capturing region calculation unit 108. Then, the acquired image-capturing region is calculated as the second image-capturing region, and becomes an image-capturing region for which image capturing is to be actually performed by the tomographic-image capturing unit 130. Then, information regarding the second image-capturing region is output to the image-capturing determination unit 150. Note that the maximum image-capturing size may be a limiting size in which the tomographic-image capturing unit 130 is able to capture images, or may simply be a size indicating an image-capturing range input by an operator.

The image-capturing determination unit 150 determines whether or not a post-treatment observation (follow-up) is possible by comparing the position information about the first image-capturing region calculated by the first image-capturing region calculation unit 104 with the position information about the second image-capturing region calculated by the second image-capturing region calculation unit 108. In other words, the image-capturing determination unit 150 determines whether or not to prohibit the tomographic-image capturing unit 130 from capturing images in accordance with a comparison between the first image-capturing region and the second image-capturing region. That is, the second image-capturing region calculation unit 108 is an example of a determination unit that determines whether or not to prohibit capturing of a second tomographic image in accordance with a comparison between the parameter regarding capturing of a first tomographic image and the parameter regarding capturing of the second tomographic image.

In the case where the image-capturing determination unit 150 has determined that a post-treatment observation is possible, the image-capturing command unit 151 issues a command for capturing a tomographic image of the second image-capturing region to the tomographic-image capturing unit 130 upon receiving an image-capturing start command input through an image-capturing switch, which is not illustrated, operated by an operator. As a result, the tomographic-image capturing unit 130 captures a tomographic image of the second image-capturing region (a second tomographic image), and this second tomographic image is stored in the image storage unit 102.

In the case where the image-capturing determination unit 150 has determined that a post-treatment observation is to be prohibited, the image-capturing determination unit 150 controls the tomographic-image capturing unit 130 such that even when an image-capturing command issued from the image-capturing command unit 151 is input to the tomographic-image capturing unit 130, the image-capturing command becomes invalid. That is, the tomographic-image capturing unit 130 is an example of an image capturing unit that captures a second tomographic image, and the image-capturing determination unit 150 is an example of a controller that controls the image capturing unit. More specifically, in the case where the determination unit has determined that capturing of a second tomographic image is to be prohibited, the image-capturing determination unit 150, which is an example of the controller, prohibits the image capturing unit from capturing images.

Note that the image-capturing controller 110 serves as the tomographic-image acquiring unit 101, the first image-capturing region calculation unit 104, the second image-capturing region calculation unit 108, the image information output unit 111, the image-capturing determination unit 150, and the image-capturing command unit 151 illustrated in FIG. 1 when a CPU, which is not illustrated, executes a program stored in a read-only memory (ROM), which is not illustrated.

Note that the number of CPUs and the number of ROMs that the image-capturing controller 110 has may be one or more than one. That is, in the case where at least one or more processing devices (CPUs) are connected to at least one storage device (ROM or the like), and at least one or more processing devices have executed a program stored in at least one or more storage units, the image-capturing controller 110 serves as the above-described units.

An operation of the image-capturing controller 110 according to the present exemplary embodiment is the above-described operation of the image-capturing determination unit 150. Details of the operation will be described in detail using FIGS. 2 and 3.

Figure 2:
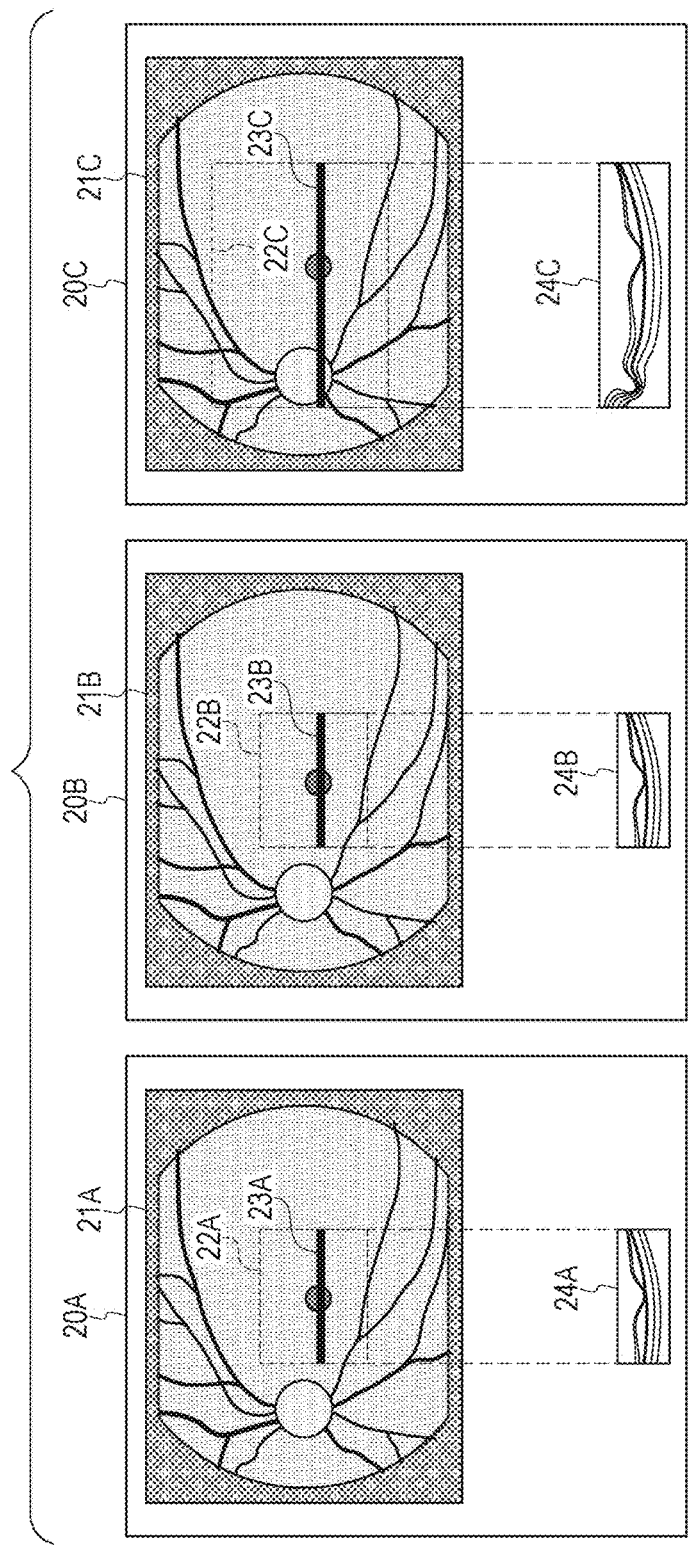
FIG. 2 is a diagram illustrating an example of a display screen of an image display unit at the time of a post-treatment observation.

FIG. 2 illustrates a display screen of the image display unit 112 at the time of post-treatment observations using the OCT. Images displayed on the image display unit 112 and denoted by 20A, 20B, and 20C are captured in the order of 20A, 20B, and 20C, and 21A, 21B, and 21C denote fundus images when the respective images 20A, 20B, and 20C are captured. Then, 22A, 22B, and 22C denote image-capturing regions when the respective images 20A, 20B, and 20C are captured. Furthermore, 24A, 24B, and 24C denote tomographic images when the respective images 20A, 20B, and 20C are captured, and 23A, 23B, and 23C indicate positions of the respective tomographic images in the respective fundus images when the respective images 20A, 20B, and 20C are captured.

For 20A and 20B, respective image-capturing regions 22A and 22B are the same in terms of position and size. That is, images have been captured by devices having the same image-capturing region in terms of size, which is a type of image-capturing performance.

However, for 20B and 20C, respective image-capturing regions 22B and 22C are not the same in size. Thus, it may be determined that images have been captured by devices whose image-capturing regions are different from each other in terms of size, which is a type of image-capturing performance.

Figure 3:
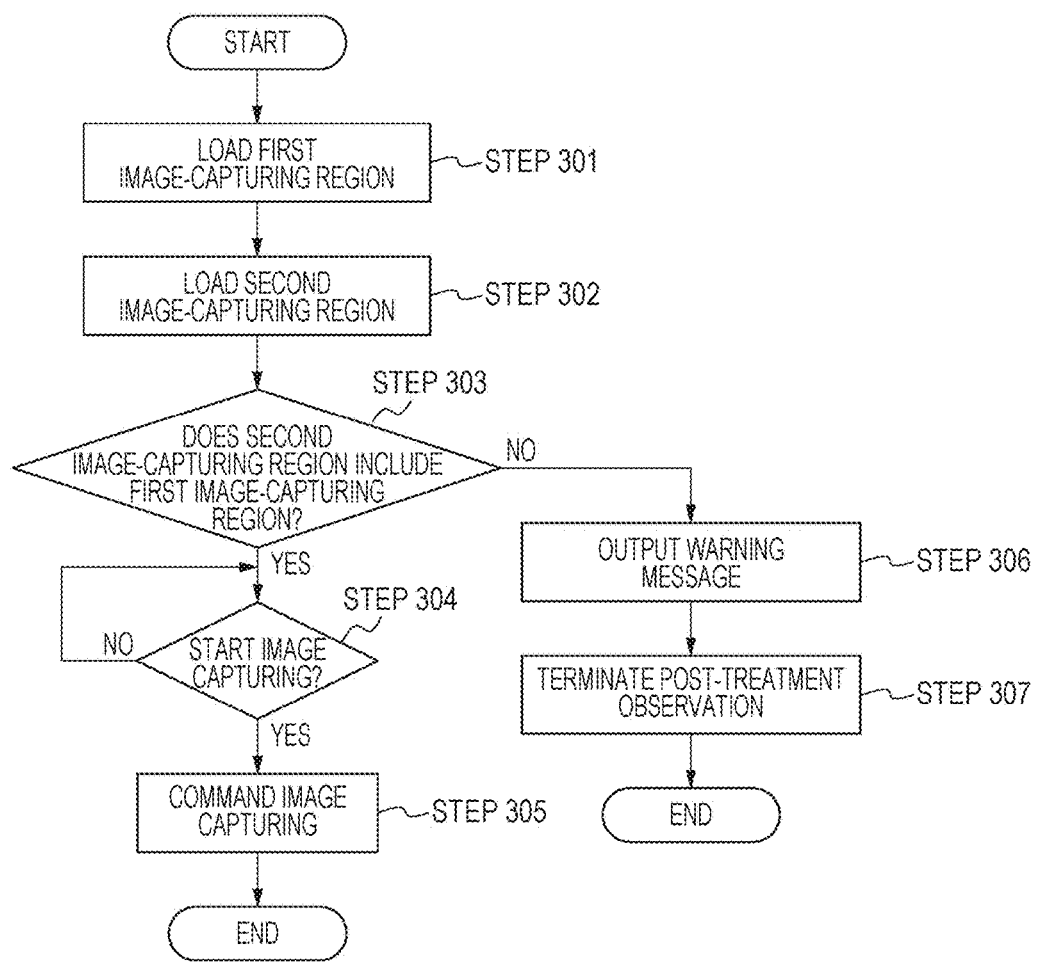
FIG. 3 is a flowchart illustrating an example of an operation procedure of an image-capturing controller according to the first exemplary embodiment.

Next, an operation of the image-capturing controller 110 according to the present exemplary embodiment will be described in detail using a flowchart of FIG. 3.

First, in step 301, the image-capturing determination unit 150 loads a first image-capturing region calculated by the first image-capturing region calculation unit 104. Next, in step 302, the image-capturing determination unit 150 loads a second image-capturing region calculated by the second image-capturing region calculation unit 108. Note that steps 301 and 302 may be executed in the opposite order.

In step 303, the image-capturing determination unit 150 compares the first image-capturing region and the second image-capturing region loaded in steps 301 and 302 with each other. In the case where the second image-capturing region includes the first image-capturing region, the process proceeds to step 304. That is, in the case where an image-capturing range for a second tomographic image includes an image-capturing range for a first tomographic image, the image-capturing determination unit 150, which is an example of the determination unit, determines that capturing of the second tomographic image is to be allowed.

The operation in and after step 304 is an operation of the image-capturing command unit 151.

Then, in step 304, it is monitored whether an operator has operated the image-capturing switch, which is not illustrated. When the image-capturing switch is operated, the process proceeds to step 305. In step 305, the image-capturing command unit 151 issues a command for capturing a tomographic image of the second image-capturing region to the tomographic-image capturing unit 130.

Here, the first image-capturing region calculated by the first image-capturing region calculation unit 104 is, as described above, an image-capturing region (first image-capturing region) for an image captured in the past and stored in the image storage unit 102. In addition, the second image-capturing region calculated by the second image-capturing region calculation unit 108 is an image-capturing region an image of which is capable of being captured using the tomographic-image capturing unit 130. That is, in the case of the relationship between 20B and 20C described using FIG. 2, processing in steps 301 to 305 is executed.

In contrast, in step 303, in the case where the second image-capturing region does not include the first image-capturing region in accordance with a result of a comparison between the first image-capturing region and the second image-capturing region, the process proceeds to step 306. In step 306, a warning unit, which is not illustrated, causes the image display unit 112 to display a warning message. Note that the operator may be notified, using the warning unit such as an unillustrated buzzer, that image capturing is unable to be performed for a post-treatment observation. That is, the warning unit, which is not illustrated, issues a warning against capturing of a second tomographic image in accordance with a comparison between a parameter regarding capturing of a first tomographic image and a parameter regarding capturing of the second tomographic image. More specifically, in the case where it is determined that capturing of a second tomographic image is to be prohibited, the warning unit, which is not illustrated, issues a warning indicating that capturing of the second tomographic image is to be prohibited. In this manner, the image-capturing determination unit 150 prohibits image capturing for a post-treatment observation. That is, in the case where an image-capturing range for a second tomographic image does not include an image-capturing range for a first tomographic image, the image-capturing determination unit 150 determines that capturing of the second tomographic image is to be prohibited.

Thereafter, in step 307, a post-treatment observation image-capturing mode is terminated.

The above-described operation performed in the case where the process proceeds from step 303 to step 306 will be described in detail using an example of post-treatment observations illustrated in FIG. 4.

Figure 4:
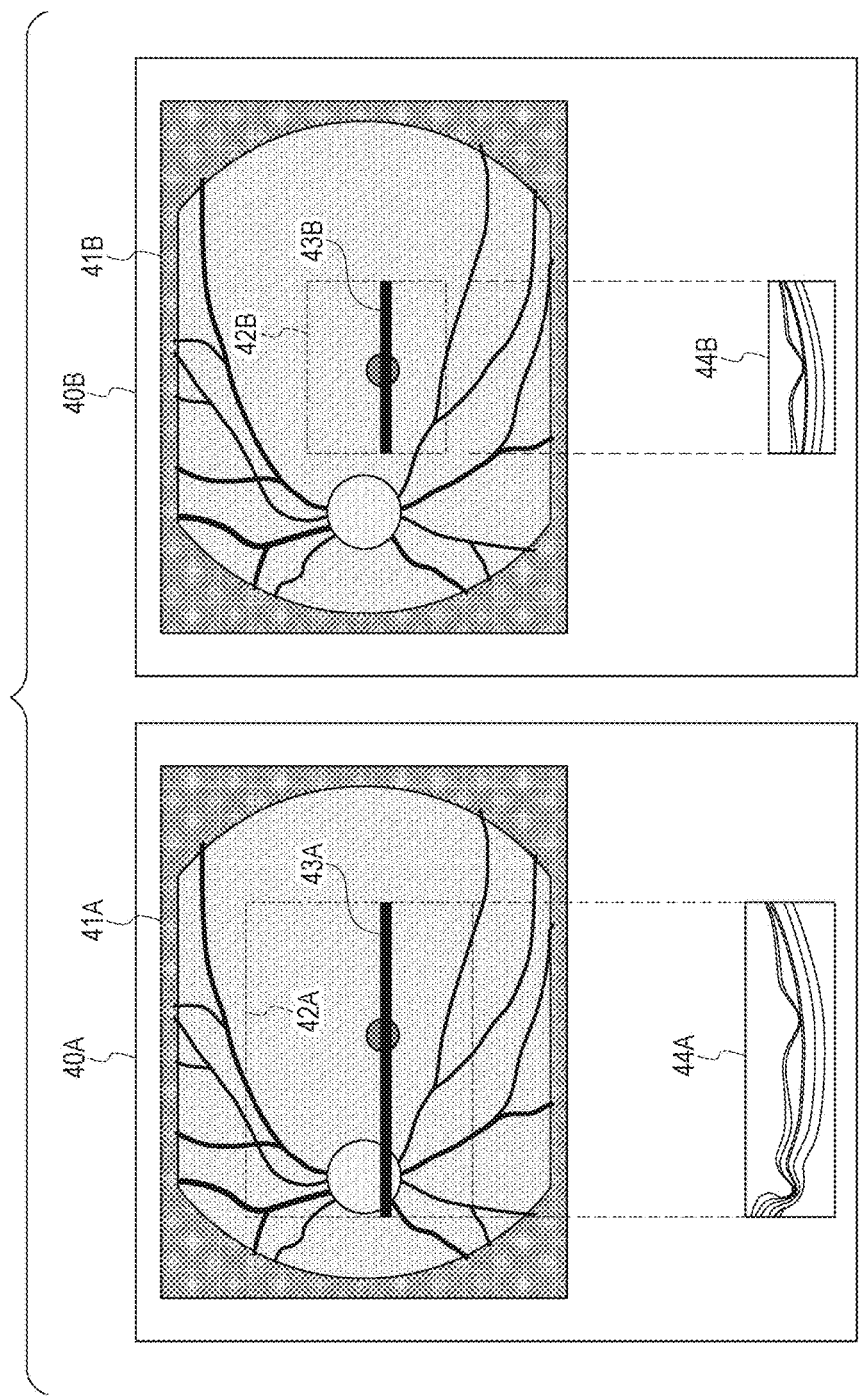
FIG. 4 is a diagram illustrating an example of a post-treatment observation.

FIG. 4 illustrates a scene of the image display unit 112 at the time of post-treatment observations using the OCT. Images displayed on the image display unit 112 and denoted by 40A and 40B are captured in the order of 40A and 40B, and 41A and 41B denote fundus images when the respective images 40A and 40B are captured. Then, 42A and 42B denote image-capturing regions when the respective images 40A and 40B are captured. Furthermore, 44A and 44B denote tomographic images when the respective images 40A and 40B are captured, and 43A and 43B indicate positions of the respective tomographic images in the respective fundus images when the respective images 40A and 40B are captured.

For 40A and 40B, respective image-capturing regions 42A and 42B are not the same in size. Furthermore, the image-capturing region 42A is larger than the image-capturing region 42B. The first image-capturing region, which is an image-capturing region for an image captured in the past, is denoted by 42A, and the second image-capturing region is an image-capturing region an image of which is capable of being captured this time is denoted by 42B. Thus, this is the case where the second image-capturing region does not include the first image-capturing region in the operation of the image-capturing controller 110 according to the flowchart of FIG. 3. That is, the process proceeds to step 306. After the operator is notified that image capturing for a post-treatment observation is unable to be performed, the post-treatment observation image-capturing mode is terminated. For example, 40A denotes an image captured by a swept-source OCT device, and 40B denotes an image captured by a spectral-domain OCT device having a smaller angle of view than the swept-source OCT device.

As described above using FIGS. 2 and 3 and FIG. 4, in the case where the first image-capturing region, an image-capturing region for an image captured in the past, is compared with the second image-capturing region an image of which is capable of being captured this time, and where a post-treatment observation is possible, the post-treatment observation is continued. In the case where a post-treatment observation is unable to be performed, the post-treatment observation is terminated.

Thus, in the case where post-treatment observations are performed using devices that differ from each other in terms of image-capturing performance, and where the last image of an eye to be examined has been captured using a device having a wide image-capturing region, it is not allowed to capture an image of the eye to be examined using a device having a narrow image-capturing region. Thus, even in the case where the operator has selected a device inappropriate for image capturing for a post-treatment observation, an image of a subject is not captured by mistake.

In this manner, according to the above-described exemplary embodiment, unnecessary image capturing may be prevented by determining whether or not a post-treatment observation is possible. That is, according to the above-described exemplary embodiment, in the case where a parameter regarding an tomographic image such as, for example, an image-capturing range or a resolution regarding image capturing performed this time is inferior to a parameter regarding image capturing performed in the past, it is possible to perform appropriate image-capturing control.

More specifically, in the case where image capturing has been performed in the past using a swept-source OCT device, and image capturing is performed for a post-treatment observation using a spectral-domain OCT device having a narrower image-capturing range than the swept-source OCT device, it is possible to prohibit image capturing. That is, in the case where a post-treatment observation may not be appropriately performed, it is possible to prohibit image capturing for a post-treatment observation. Thus, according to the present exemplary embodiment, the burden of a subject may be prevented from increasing by avoiding unnecessary image capturing.

Note that even in the case where a post-treatment observation is performed using tomographic images captured using the same method, when a parameter regarding image capturing is inferior to a parameter regarding image capturing performed in the past, image capturing may be prohibited. In this manner, too, it is possible to obtain effects substantially the same as above.

Figure 5:
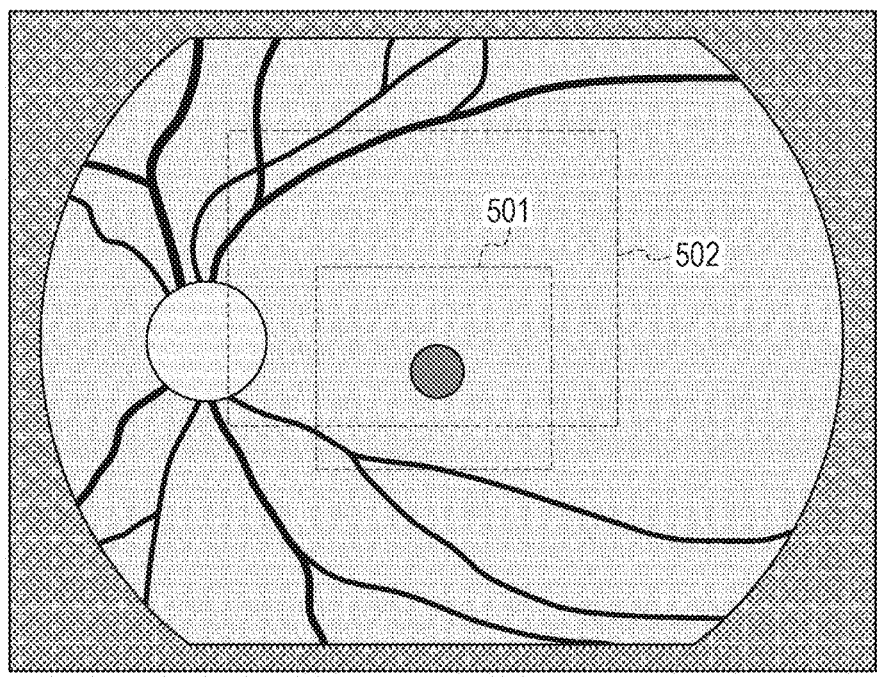
FIG. 5 is a diagram illustrating an example of the relationship between image-capturing regions.

In the present exemplary embodiment, the post-treatment observation image-capturing mode is terminated after step 306. However, since it is determined in step 303 that the second image-capturing region does not include the first image-capturing region, for example, there may be a case where, as illustrated in FIG. 5, a second image-capturing region 502 has been moved to a position at which the second image-capturing region 502 does not include a first image-capturing region 501. In such a case, the post-treatment observation image-capturing mode may not be terminated, and the operator may be instructed to change the range of the second image-capturing region 502 again.

Second Exemplary Embodiment

In the first exemplary embodiment, in the case where a post-treatment observation is performed using devices that differ from each other in terms of image-capturing performance, prevention of unnecessary image capturing has been described using the example in which an image of an eye to be examined is captured using a device having a narrow image-capturing region, the eye to be examined having been subjected to image capturing using a device having a wide image-capturing region the last time.

In a second exemplary embodiment, although similarly to as in the first exemplary embodiment, there may be a case where image capturing is possible for a post-treatment observation. The configuration of an apparatus that makes it possible to perform such an operation will be described. In addition, in the second exemplary embodiment, reference numerals the same as those of the first exemplary embodiment denote the same elements as those of the first exemplary embodiment.

Figure 6:
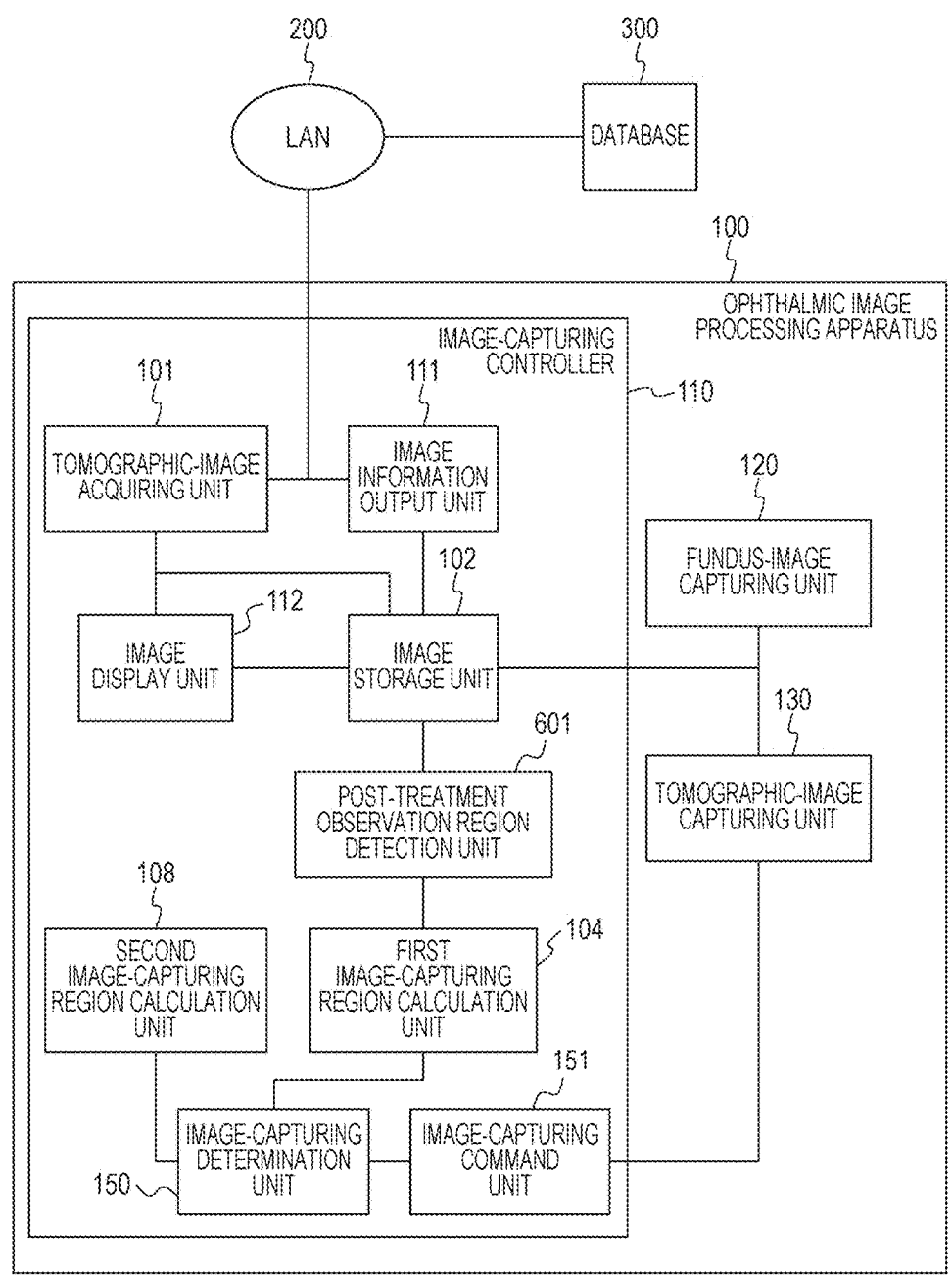
FIG. 6 is a diagram illustrating an example of the configuration of an ophthalmic image processing apparatus according to a second exemplary embodiment.

FIG. 6 is a schematic diagram illustrating an example of a schematic configuration of the eye-portion image capturing system 10 according to the second exemplary embodiment of the present invention.

In comparison with the configuration of FIG. 1, the image-capturing controller 110 includes a post-treatment observation region detection unit 601 between the image storage unit 102 and the first image-capturing region calculation unit 104. The post-treatment observation region detection unit 601 is configured to detect a post-treatment observation region in an image recorded in the image storage unit 102, and output the detected post-treatment observation region to the first image-capturing region calculation unit 104.

Next, an operation of the eye-portion image capturing system 10 illustrated in FIG. 6 will be described in detail using FIG. 7.

Figure 7:
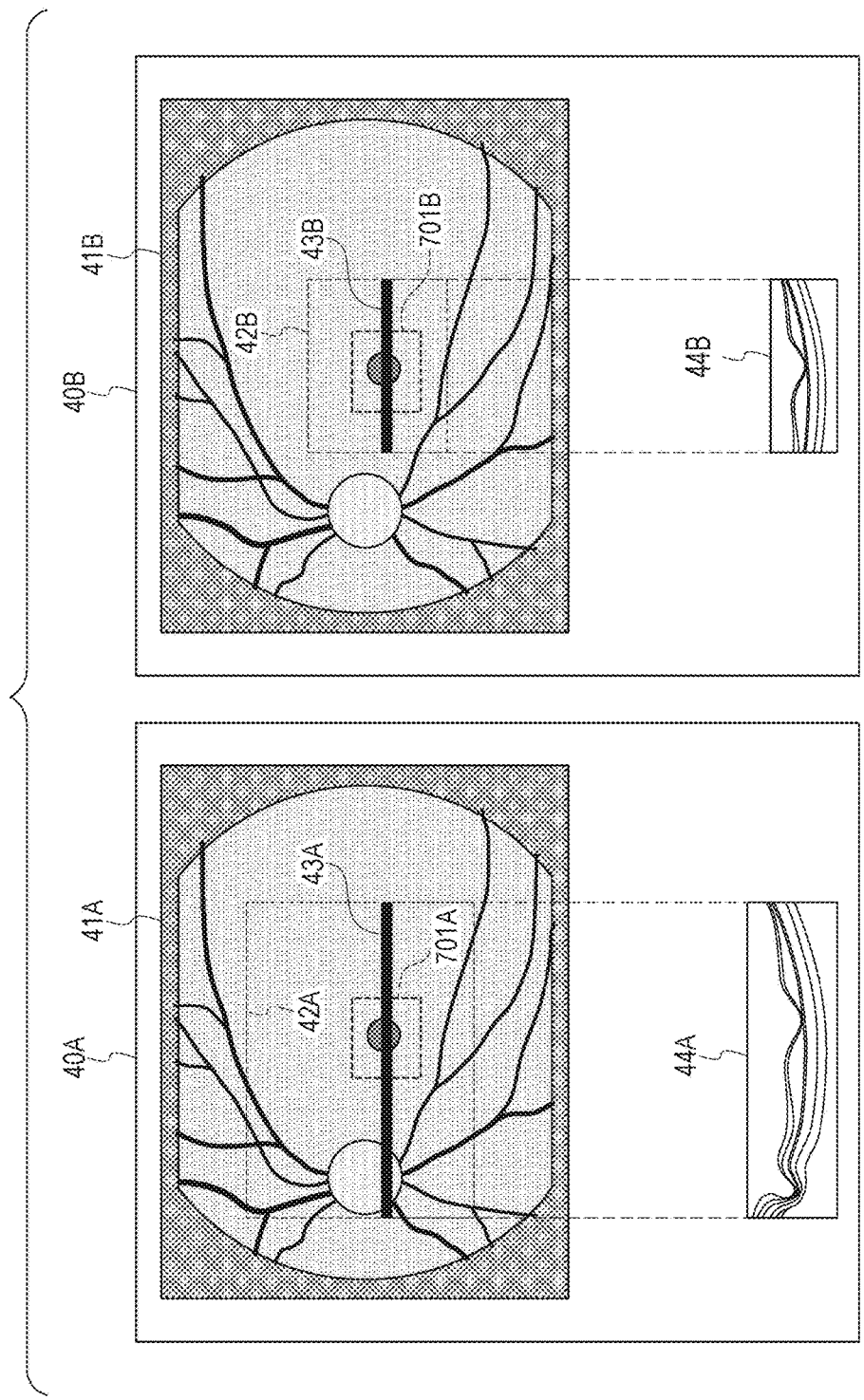
FIG. 7 is a diagram illustrating an example of a display screen of an image display unit at the time of a post-treatment observation according to the second exemplary embodiment.

FIG. 7 illustrates, similarly to as in FIG. 4, a scene of post-treatment observations in the case where a first image-capturing region, which is an image-capturing region for an image captured in the past, is denoted by 42A, and a second image-capturing region is an image-capturing region an image of which is capable of being captured this time is denoted by 42B. That is, this is an example of the case where it is determined in the first exemplary embodiment that a post-treatment observation is unable to be performed since the second image-capturing region does not include the first image-capturing region. For example, similarly to as in the first exemplary embodiment, the first image-capturing region 42A shows an image-capturing region of a swept-source OCT device, and the second image-capturing region 42B shows an image-capturing region of a spectral-domain OCT device. Note that the first image-capturing region 42A and the second image-capturing region 42B may show different image-capturing ranges of the same OCT.

However, in the case where the first image-capturing region 42A includes a post-treatment observation region 701A, since the same region as the post-treatment observation region 701A is a post-treatment observation region 701B in the second image-capturing region 42B, the post-treatment observation region 701B is included in the second image-capturing region 42B. Thus, even in the case where it is determined in the first exemplary embodiment that a post-treatment observation is unable to be performed, there is no problem about performance of a post-treatment observation.

In such a case, it is effective to detect the post-treatment observation region 701A in the post-treatment observation region detection unit 601 described using FIG. 6. Here, as a post-treatment observation region detection method performed by the post-treatment observation region detection unit 601, a method for detecting a portion of interest input through an unillustrated input unit by the operator may be used. In addition, a post-treatment observation region may also be detected in accordance with the type of a scan mode in which a characteristic portion of a fundus (a characteristic portion of an eye to be examined) such as a macula lutea or an optic disc is treated as a target. Note that the characteristic portion is not limited to the macula lutea or the optic disc, and the characteristic portion may also be a blood vessel portion, a lesion portion, or the like. For example, in the case where a macula lutea mode is associated as a scan mode with a tomographic image captured in the past, the post-treatment observation region detection unit 601 determines that an observation region is a macula lutea. This configuration makes it possible to detect the post-treatment observation region 701A. The first image-capturing region calculation unit 104 confirms whether or not the post-treatment observation region 701A is included in the first image-capturing region 42A. For example, the first image-capturing region calculation unit 104 determines whether or not the post-treatment observation region 701A, which is a macula lutea, is included in the image-capturing region 42A on the fundus image 41A. In the case where a macula lutea is included in the image-capturing region 42A, the post-treatment observation region detection unit 601 determines whether or not a macula lutea is included in the image-capturing region 42B. For example, the post-treatment observation region detection unit 601 extracts the macula lutea from the image-capturing region 42B in the fundus image 41B. Since the brightness of a macula lutea is lower than the brightness of its surroundings in a fundus image, it is possible to detect a macula lutea by, for example, extracting a low-brightness region. In the case where an optic disc is to be detected, a high-brightness region is extracted. In the case where a macula lutea has been detected in the image-capturing region 42B, even when the post-treatment observation region 701A is not included in the post-treatment observation region 701B, it is possible to perform a post-treatment observation for a portion of interest. Thus, the image-capturing determination unit 150 determines that image capturing is to be allowed. As the operation of the image-capturing controller 110 according to the flowchart of FIG. 3, a process in which the image-capturing determination unit 150 determines whether or not the post-treatment observation region 701B corresponding to the post-treatment observation region 701A is included in the image-capturing region 42B is added between steps 303 and 306. In the case where the image-capturing determination unit 150 has determined that the post-treatment observation region 701B is included in the image-capturing region 42B, the process proceeds to step 304. In the case where it has been determined that the post-treatment observation region 701B is not included in the image-capturing region 42B, the process proceeds to step S306. That is, in the case where an image-capturing range for a second tomographic image does not include an image-capturing range for a first tomographic image, the determination unit further determines whether or not a characteristic portion of an eye to be examined included in part of the image-capturing range for the first tomographic image is included in the image-capturing range for the second tomographic image. In the case where the characteristic portion of the eye to be examined is included in the image-capturing range for the second tomographic image, the determination unit determines that capturing of the second tomographic image is to be allowed.

Then, in step 304, it is monitored whether the operator has operated the image-capturing switch, which is not illustrated. When the image-capturing switch is operated, the process proceeds to step 305. In step 305, a command for capturing a tomographic image of the second image-capturing region is issued to the tomographic-image capturing unit 130.

According to the present exemplary embodiment, even in the case where an image-capturing range used this time does not include an image-capturing range used in the past, when a portion of interest, which is a post-treatment observation target, is included in the image-capturing range used this time, it is possible to perform image capturing. Therefore, in the case where a post-treatment observation is performed using devices that differ from each other in terms of the image-capturing range, image capturing may be prevented from being prohibited all the time, and it is possible to improve the operator's degree of freedom. Note that a captured tomographic image may be associated with information indicating that image capturing has been performed using a device whose method is different from that used in image capturing performed the last time (image capturing performed in the past).

Third Exemplary Embodiment

In the first exemplary embodiment, in the case where a post-treatment observation is performed using devices that differ from each other in terms of image-capturing performance, prevention of unnecessary image capturing has been described using the example in which an image of an eye to be examined is captured using a device having a narrow image-capturing region, the eye to be examined having been subjected to image capturing using a device having a wide image-capturing region the last time.

In a third exemplary embodiment, a case will be described where image capturing for a post-treatment observation is prohibited by comparing parameters regarding capturing of images other than parameters regarding image-capturing regions. In addition, in the third exemplary embodiment, reference numerals the same as those of the first exemplary embodiment denote the same elements as those of the first exemplary embodiment.

Figure 8:
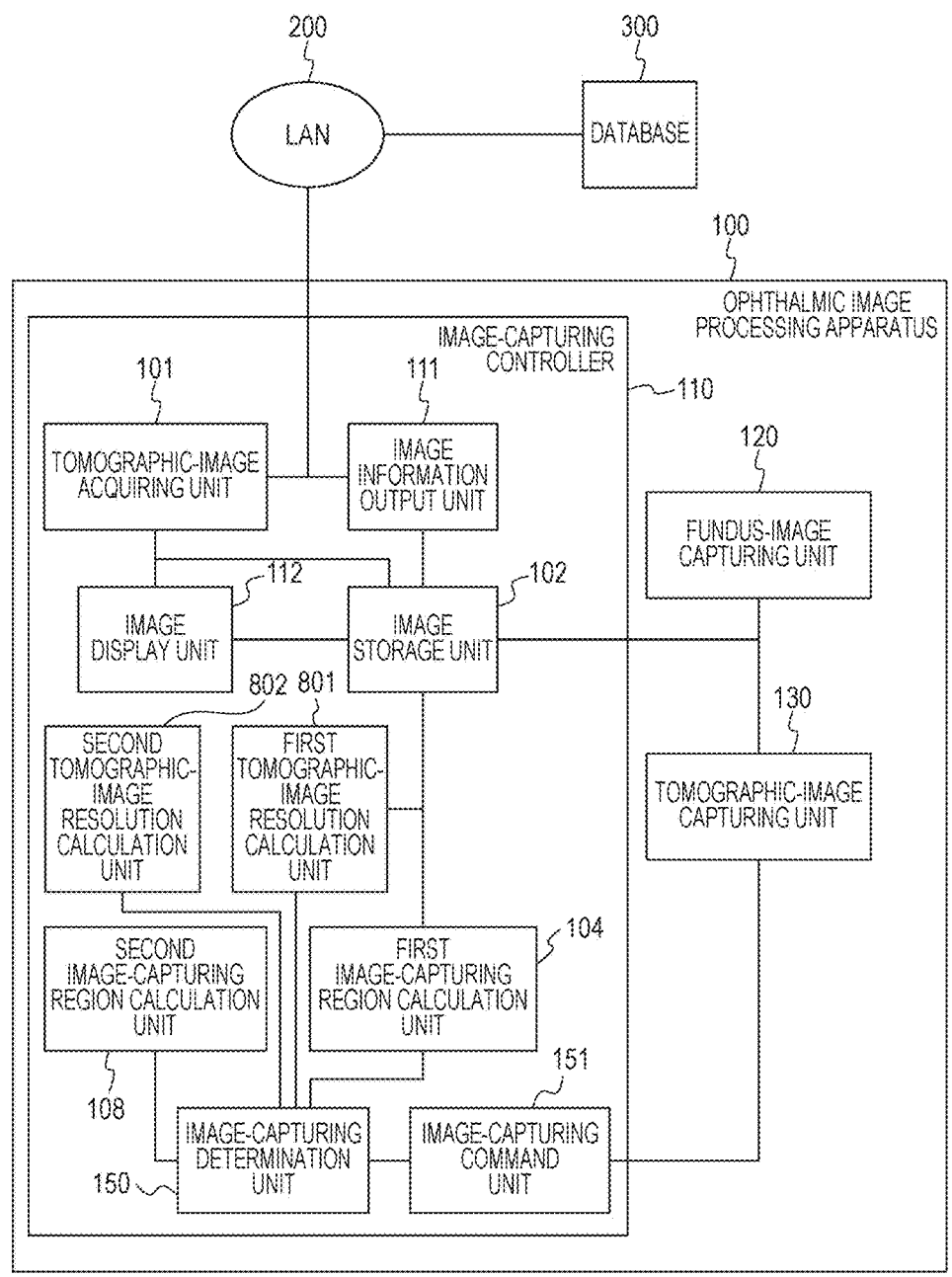
FIG. 8 is a diagram illustrating an example of the configuration of an ophthalmic image processing apparatus according to a third exemplary embodiment.

FIG. 8 is a schematic diagram illustrating an example of a schematic configuration of the eye-portion image capturing system 10 according to the third exemplary embodiment.

Compared with the configuration of FIG. 1, the image-capturing controller 110 includes a first tomographic-image resolution detection unit 801 and a second tomographic-image resolution detection unit 802.

Here, the first tomographic-image resolution detection unit 801 is configured to detect a tomographic image resolution from images recorded in the image storage unit 102, and to output the detected tomographic image resolution to the image-capturing determination unit 150. Note that the first tomographic-image resolution detection unit 801 detects at least one of a horizontal resolution and a vertical resolution. The first tomographic-image resolution detection unit 801 may detect a resolution by analyzing a tomographic image recorded in the image storage unit 102, or may acquire information regarding a resolution of a certain device that has captured a tomographic image recorded in the image storage unit 102 (spec information regarding the device).

In addition, the second tomographic-image resolution detection unit 802 is configured to detect a tomographic image resolution in which image capturing is possible this time, and output the detected tomographic image resolution to the first image-capturing region calculation unit 104. Note that the second tomographic-image resolution detection unit 802 detects at least one of a horizontal resolution and a vertical resolution. In addition, the second tomographic-image resolution detection unit 802 acquires information regarding a resolution that the tomographic-image capturing unit 130 has. For example, the information regarding the resolution that the tomographic-image capturing unit 130 has is stored in the image storage unit 102 or other storage devices.

Next, an operation of the image-capturing controller 110 having a configuration of FIG. 8 and according to the third exemplary embodiment will be described in detail using FIGS. 9 and 10.

Figure 9:
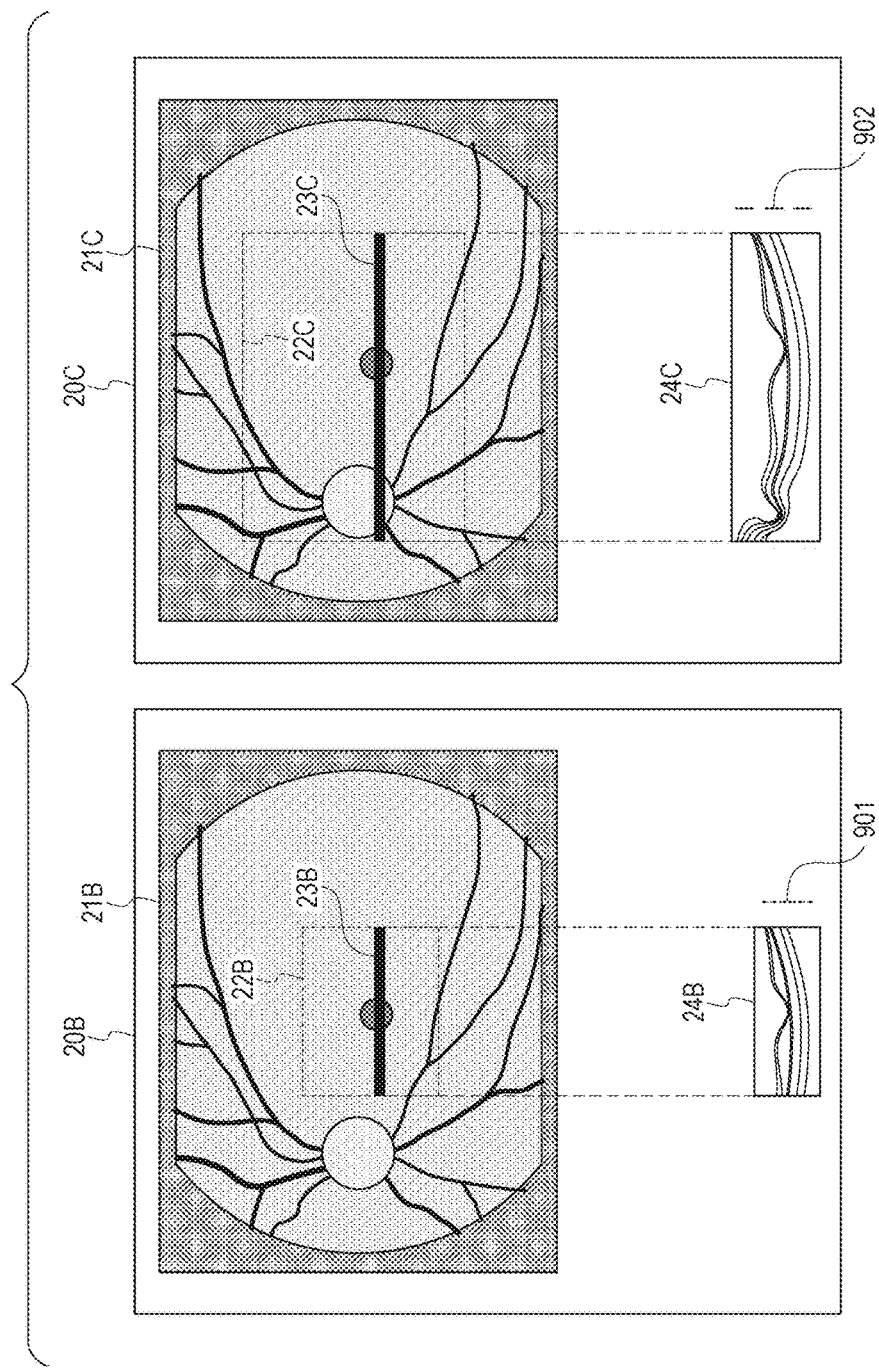
FIG. 9 is a diagram illustrating an example of a display screen of an image display unit at the time of a post-treatment observation according to the third exemplary embodiment.

FIG. 9 illustrates, similarly to as in FIG. 2, a scene of post-treatment observations in the case where the first image-capturing region, which is an image-capturing region for an image captured in the past, is denoted by 22B, and the second image-capturing region is an image-capturing region an image of which is capable of being captured this time is denoted by 22C. Here, 20B denotes image capturing performed in the past, and 20C denotes image capturing performed this time. In addition, 21B and 21C denote fundus images. This is an example of the case where it is determined in the first exemplary embodiment that a post-treatment observation is possible since the second image-capturing region includes the first image-capturing region.

However, in the present exemplary embodiment, in the case where a resolution 901 of a tomographic image 24B of the first image-capturing region 22B is higher than a resolution 902 of a tomographic image 24C of the second image-capturing region 22C, image capturing is to be prohibited. This is because there may be a case where a retinal layer capable of being observed in the tomographic image 24B may not be observed in the tomographic image 24C. Thus, even in the case where it is determined in the first exemplary embodiment that a post-treatment observation is possible, a post-treatment observation is prohibited from being performed in the present exemplary embodiment.

Figure 10:
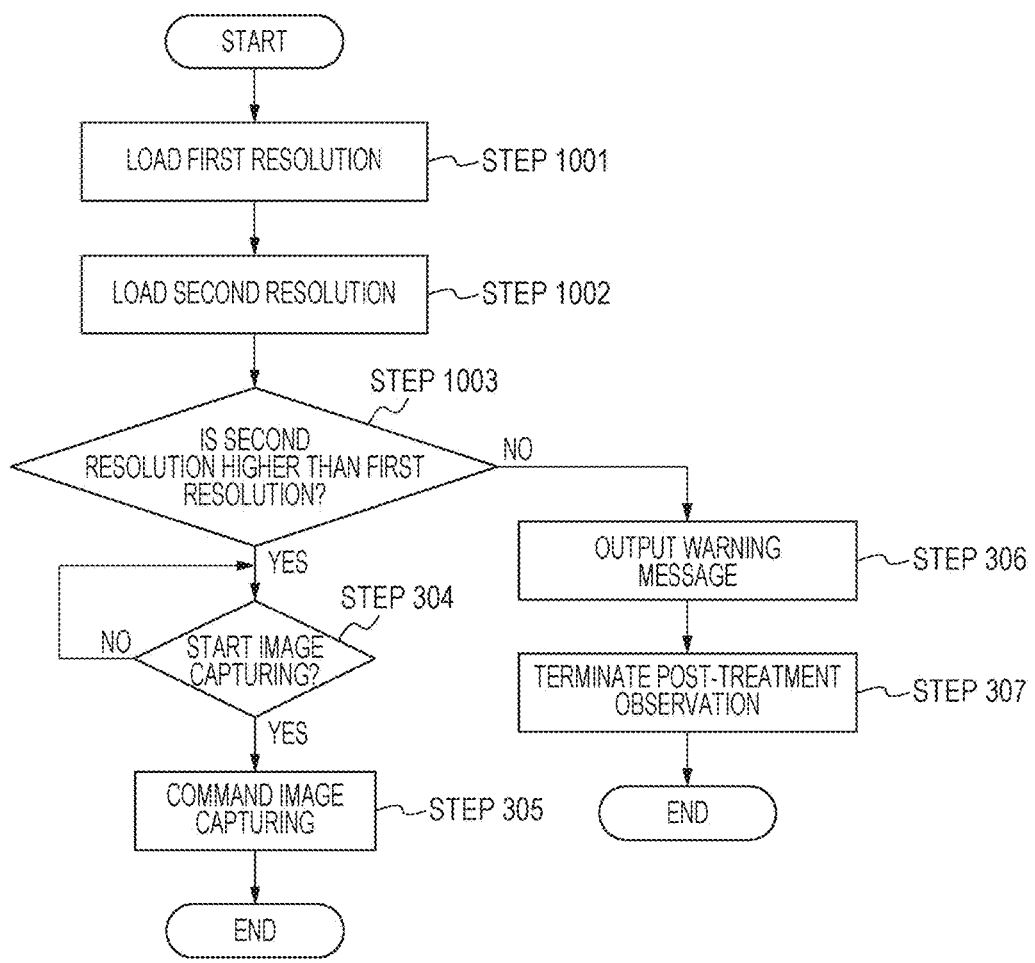
FIG. 10 is a flowchart illustrating an example of an operation procedure of an image-capturing controller according to the third exemplary embodiment.

FIG. 10 illustrates an example of an operation procedure of the image-capturing controller 110 in the present exemplary embodiment. First, in step 1001, the first tomographic-image resolution detection unit 801 detects the resolution of a tomographic image recorded in the image storage unit 102. The resolution detected in step 1001 is treated as a first resolution. Next, in step 1002, the second tomographic-image resolution detection unit 802 detects a resolution that the tomographic-image capturing unit 130 has. The resolution detected in step 1002 is treated as a second resolution.

In step 1003, the image-capturing determination unit 150 compares the first resolution with the second resolution. Specifically, it is determined whether the second resolution is higher than the first resolution or whether the second resolution is higher than or equal to the first resolution. In the case where the second resolution is higher than the first resolution or where the second resolution is higher than or equal to the first resolution, the process proceeds to step 304. That is, in the case where the resolution regarding capturing of a second tomographic image is higher than the resolution of a first tomographic image, the image-capturing determination unit 150, which is an example of the determination unit, determines that capturing of the second tomographic image is to be allowed.

In contrast, in the case where the second resolution is lower than the first resolution, the process proceeds to step 306. That is, in the case where the resolution regarding capturing of a second tomographic image is lower than the resolution of a first tomographic image, the image-capturing determination unit 150, which is an example of the determination unit, prohibits capturing of the second tomographic image.

Note that the processes in and after steps 304 and 306 are substantially the same as those of the first exemplary embodiment, and thus description thereof will be omitted.

According to the present exemplary embodiment, it is possible to obtain effects substantially the same as those of the first exemplary embodiment. A resolution is focused in the present exemplary embodiment; however, what is focused is not limited to this. Other parameters regarding image capturing may also be used to control image capturing in a post-treatment observation.

Note that step 1003 may be executed between steps 303 and 304. That is, the first exemplary embodiment and the third exemplary embodiment may be combined. Note that the first and second exemplary embodiments and the third exemplary embodiment may also be combined.

In addition, steps 1001 and 1002 may be executed in the order opposite to that of the example illustrated in FIG. 10.

Note that as a tomographic-image resolution detection method performed by the first tomographic-image resolution detection unit 801, a method for reading out device information prerecorded in captured-image information obtained by performing image capturing the last time may be used. In addition, a tomographic image resolution may also be detected from the vertical display range and the resolution of a certain tomographic image.

OTHER EMBODIMENTS

Additional embodiments can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiments and/or that includes one or more circuits (e.g., application specific integrated circuit (ASIC)) for performing the functions of one or more of the above-described embodiments, and by a method performed by the computer of the system or apparatus by, for example, reading out and executing the computer executable instructions from the storage medium to perform the functions of one or more of the above-described embodiments and/or controlling the one or more circuits to perform the functions of one or more of the above-described embodiments. The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that these exemplary embodiments are not seen to be limiting. The scope of the following claims is to be accorded the broadest interpretation so as to encompass all such modifications and equivalent structures and functions.

This application claims the benefit of Japanese Patent Application No. 2015-002517, filed Jan. 8, 2015, which is hereby incorporated by reference herein in its entirety.

What is claimed is:

1. An ophthalmic apparatus including a program stored in a non-transitory memory and executable by a processor comprising:

a first acquiring module configured to acquire a parameter regarding capturing of a first tomographic image of an eye to be examined, the parameter including a resolution, wherein the first tomographic image is a tomographic image already captured;

a second acquiring module configured to acquire a parameter regarding capturing of a second tomographic image of the eye to be examined, wherein the second tomographic image is a tomographic image to be captured and capturing of the second tomographic image is being performed after capturing of the first tomographic image;

a determination module configured to compare the parameter regarding capturing of the first tomographic image with the parameter regarding capturing of the second tomographic image, wherein the comparing by the determination module is performed before the second tomographic image is captured and after the first tomographic image is captured; and a warning module configured to issue a warning, in a case where a resolution regarding capturing of the second tomographic image is lower than a resolution of the first tomographic image, against capturing of the second tomographic image in accordance with a result of a comparison by the determination module, wherein the warning module issues the warning before the second tomographic image is captured and after the first tomographic image is captured.

2. The ophthalmic apparatus according to claim 1, wherein the parameter includes an image-capturing range, and the warning module issues the warning in a case where an image-capturing range for the second tomographic image does not include an image-capturing range for the first tomographic image.

3. The ophthalmic apparatus according to claim 2, wherein the warning module does not issue the warning in a case where the image-capturing range for the second tomographic image includes an image-capturing range for the first tomographic image.

4. The ophthalmic apparatus according to claim 1, wherein the warning module does not issue the warning in a case where the resolution regarding capturing of the second tomographic image is higher than the resolution of the first tomographic image.

5. The ophthalmic apparatus according to claim 1, further comprising a second determination module configured to determine whether or not to prohibit capturing of the second tomographic image in accordance with a comparison between the parameter regarding capturing of the first tomographic image and the parameter regarding capturing of the second tomographic image.

6. The ophthalmic apparatus according to claim 5, further comprising:

an image capturing module configured to capture the second tomographic image; and a control module configured to control the image capturing unit, wherein in a case where the second determination module has determined that capturing of the second tomographic image is to be prohibited, the control module prohibits the image capturing module from capturing an image.

7. The ophthalmic apparatus according to claim 1, wherein in a case where an image-capturing range for the second tomographic image does not include an image-capturing range for the first tomographic image, it is further determined whether or not a characteristic portion of the eye to be examined included in part of the image-capturing range for the first tomographic image is included in the image-capturing range for the second tomographic image, and the warning module does not issue the warning in a case where the characteristic portion of the eye to be examined is included in the image-capturing range for the second tomographic image.

8. A control method using a non-transitory memory that stores a program of instructions and using a processor that executes the program of instructions to perform the control method, the control method comprising:
acquiring a parameter regarding capturing of a first tomographic image of an eye to be examined, the parameter including a resolution, the first tomographic image being a tomographic image already captured;
acquiring a parameter regarding capturing of a second tomographic image of the eye to be examined, the second tomographic image being a tomographic image to be captured and the image capturing being performed after capturing of the first tomographic image;
determining a comparison of the parameter regarding capturing of the first tomographic image with the parameter regarding capturing of the second tomographic image, wherein the determining is performed before the second tomographic image is captured and after the first tomographic image is captured; and
issuing a warning, in a case where a resolution regarding capturing of the second tomographic image is lower than a resolution of the first tomographic image, against capturing of the second tomographic image in accordance with a result of the determining between the parameter regarding capturing of the first tomographic image and the parameter regarding capturing of the second tomographic image, wherein the warning is issued before the second tomographic image is captured and after the first tomographic image is captured.

9. A non-transitory computer-readable storage medium storing computer-executable instructions for causing a computer to execute a control method comprising:
acquiring a parameter regarding capturing of a first tomographic image of an eye to be examined, the parameter including a resolution, the first tomographic image being a tomographic image already captured; acquiring a parameter regarding capturing of a second tomographic image of the eye to be examined, the second tomographic image being a tomographic image to be captured and wherein capturing of the second tomographic image is being performed after capturing of the first tomographic image;
determining a comparison of the parameter regarding capturing of the first tomographic image with the parameter regarding capturing of the second tomographic image, wherein the determining is performed before the second tomographic image is captured and after the first tomographic image is captured; and
issuing a warning, in a case where a resolution regarding capturing of the second tomographic image is lower than a resolution of the first tomographic image, against capturing of the second tomographic image in accordance with a result of the determining between the parameter regarding capturing of the first tomographic image and the parameter regarding capturing of the second tomographic image, wherein the warning is issued before the second tomographic image is captured and after the first tomographic image is captured.

* * * * *